United States Patent [19]
Campisi et al.

[11] Patent Number: 5,965,543
[45] Date of Patent: Oct. 12, 1999

[54] SENESCENCE RESPONSIVE TRANSCRIPTIONAL ELEMENT

[75] Inventors: Judith Campisi; Alessandro Testori, both of Berkeley, Calif.

[73] Assignee: Geron Corporation, Menlo Park, Calif.

[21] Appl. No.: 08/840,887

[22] Filed: Apr. 17, 1997

Related U.S. Application Data

[60] Provisional application No. 60/015,813, Apr. 18, 1996.

[51] Int. Cl.⁶ .................................................. A61K 35/00
[52] U.S. Cl. .......................... 514/44; 536/24.1; 536/24.3; 536/24.31
[58] Field of Search ................................... 435/6; 536/24, 536/24.1, 24.3, 24.31; 514/44

[56] References Cited

U.S. PATENT DOCUMENTS 5,744,300   4/1998   Linskens et al. ............................ 435/6

OTHER PUBLICATIONS

Burke, Elizabeth M., et al. (1994) Altered Transcriptional Regulation of Huan Interstitial Collagenase in Cultured Skin Fibroblasts From Older Donors *Experimental Gerontol.*, 29(1):37–53.

D'Armiento, J. et al. (1992) "Collagenase Expression in the Lungs of Transgenic Mice Causes Pulmonary Emphysema", *Cell*, 71:955–961.

van der Kraan, P.M. (1990) *J. Exp. Path.* 71:19–31.

D'Armiento, J., et al. (1995) "Collagenase Expression in Transgenic MouseSkin Causes Hyperkeratosis and Acanthosis and Increases Susceptibility to Tumorigenesis" *Molec. and Cell Biol.* 15:5732–5739.

Angel, Peter, et al. (1987) "12–O–Tetradecanoyl–Phorbol–13–Acetate Induction of the Human Collagenase Gene is Mediated by an Inducible Enhancer Element Located in the 5'–Flanking Region", *Molec. and Cell Biol.* 7:2256–2266.

Campisi, Judith (1996) "Replicative Senescence: An Old Live's Tale?", *Cell* 84:497–500.

Imai, Shin–Ichiro, et al. (1994) "Immortalization–Susceptible Elements and Their Binding Factors Mediate Rejuvenation of Regulation of the Type 1 Collagenase Gene in Simian Virus 40 Large T Antigen–Transformed Immortal Human Fibroblasts", *Molecular and Cellular Biology*, 14(11):7182–7194.

Campisi, Judith (1997) "Aging and Cancer: The Double–Edged Sword of Replicative Senescence", *JAGS*, 45:1–6.

Itzhaki et al. Proc. Natl. Acad. Sci. vol. 91, pp. 8925–8929, Sep. 1994.

Sottile et al. J. Cell Physiol. vol. 138, pp. 281–290, 1989.

West et al. Exp. Cell Res. vol. 184, pp. 138–147, 1989.

*Primary Examiner*—James Ketter
*Assistant Examiner*—Irem Ycel
*Attorney, Agent, or Firm*—John R. Storella; Melya J. Hughes; Kevin R. Kaster

[57] ABSTRACT

Recombinant polynucleotides have expression control sequences that have a senescence responsive element and a minimal promoter, and which are operatively linked to a heterologous nucleotide sequence. The molecules are useful for achieving high levels of expression of genes in senescent cells. Methods of inhibiting expression of genes in senescent cells also are provided.

12 Claims, 4 Drawing Sheets

| | | FOLD ACTIVITY OVER MINIMAL PROMOTER | INCREMENTAL INCREASE |
|---|---|---|---|
| PGL-34 | —▭ | 1.0 | 0 |
| PGL-134 | ——▭ | 20.8 | 20.8 |
| PGL-390 | ———▭ | 62.5 | 3 |
| PGL-522 | ————▭ | 93.04 | 0.5 |
| PGL-522 Δ34/134 | ———∨▭ | 2.9 | N/A |
| PGL-1210 | —————▭ | 92.8 | N/A |

FIG. 3.

```
POSITION -134|              -120|         -110|
         5'   AGTC ACCATTTCTA    ATGATTGCCT    AGTCTATTCA

-90|                  -70|        -60|
TAGCTAATCA   AGAGGATGTT ATAAAGCATG  AGTCAGACAC    CTCTGGCTTT

-40|
CTGGAAGGGC   AAGGACT   3'
```

FIG. 4.

5'-FLANK COLLAGENASE
```
            -520         -510         -500         -490
       AATAGGG TACCAGGCAG CTTAACAAAG GCAGAAGGGA ACCTCAGAGA
            KpnI
-480         -470         -460         -450         -440
ACCCCGAAGA GCCACCGTAA AGTGAGTGCT GGGGGAGCTG AACTTCAGTC

-430         -420         -410         -400         -390
AGTACAGGAG CCGAACAGCC ATCAGGTGCG CAGTGTTAGT AATTCCACCC
                               AosI
-380         -370         -360         -350         -340
TCTGCCCTGG GAGCAAGGTG TGTGGAGAAA CCTGTAGCAC TTTATGACCA

-330         -320         -310         -300         -290
TCAGAACCAG CCTTTTTCAA AAAGACCATG GAGTACTCTT TGACCTGTGT
                                     ScaI
-280         -270         -260         -250         -240
ATATAACAAG AACCTTTCTC AAATAGGAAA GAAATGAATT GGAGAAAACC

-230         -220         -210         -200         -190
ACTGTTTACA TGGCAGAGTG TGTCTCCTTC GCACACATCT TGTTTGAAGT

-180         -170         -160         -150         -140
TAATCATGAC ATTGCAACAC CAAGTGATTC CAAATAATCT GCTAGGAGTC

-130         -120         -110         -100         -90
ACCATTTCTA ATGATTGCCT AGTCTATTCA TAGCTAATCA AGAGGATGTT
HphI                                               FokI
-80          -70          -60          -50          -40
ATAAAGCATG AGTCAGACAC CTCTGGCTTT CTGGAAGGGC AAGGACTCTA

-30          -20          -10    *     *    10           20
TATATACAGA GGGAGCTTCC TAGCTGGGAT ATTGGAGCAG CAAGAGGCTG 30           40           50           60           70
GGAAGCCATC ACTTACCTTG CACTGAGAAA GAAGACAAAG GCCAGTATGC 80           90          100          110          120
ACAGCTTTCC TCCACTGCTG CTGCTGCTGT TCTGGGGTGT GGTGTCTCAC 130          140          150          160          170
AGCTTCCCAG CGACTCTAGA AACACAAGAG CAAGATGTGG ACTTAGTCCA S
                XbaI
```

FIG. 5.

# SENESCENCE RESPONSIVE TRANSCRIPTIONAL ELEMENT

CROSS-REFERENCE TO RELATED APPLICATION

This application claims the benefit of the filing date of United States provisional patent application 60/015,813, filed Apr. 18, 1996, incorporated herein by reference in its entirety.

FEDERALLY SPONSORED RESEARCH OR DEVELOPMENT

Certain work described herein was supported by grant no. DEA-AC03-76SF00098 between the United States Department of Energy and the University of California for the operation of Lawrence Berkeley Laboratory. The Government may have certain rights in this invention.

BACKGROUND OF THE INVENTION

This invention relates to the field of regulation of gene expression.

Animal cells undergo replicative senescence—age-dependent decrements in function and integrity. One aspect of replicative senescence is that cells have a finite replicative life-span. After undergoing a limited number of mitotic divisions, they can no longer divide. Upon replicative senescence, cells stably arrest growth with a G1 DNA content, irreversibly losing the ability to enter S phase in response to physiologic mitogens. Another aspect of replicative senescence is that senescent cells acquire altered functions, resembling terminally differentiated cells. A third aspect of replicative senescence is that senescent cells acquire resistance to apoptotic cell death.

Senescent cells exhibit altered gene expression compared with pre-senescent cells. In particular, several genes increase expression. For example, senescent human fibroblasts show a marked increase in interstitial collagenase mRNA and protein. Burke et al., Exp. Gerontol., (1994) 29:37–53. Senescent cells also exhibit increased expression of stromelysin, the adhesion molecule ICAM, and certain inflammatory mediators, such as IL-1. Other genes, such as certain mitogen inducible genes and IL-6, are repressed in senescent cells. Altered gene expression manifests itself at the tissue and organismic level.

For example, collagenase breaks down collagen, particularly, the fibrillar collagens (types I, II and III). The extracellular matrix is made of a complex network of proteins and proteoglycans, including collagen, that maintain the integrity of tissues. J. D'Armiento et al., Cell, (1992) 71:955–961. The turnover of these molecules is effected by, among other things, matrix metalloproteinases such as interstitial collagenase. Interstitial collagenase has been implicated in osteoarthritis, periodontal lesions, bullous skin lesions, cancer invasion and a variety of liver and lung diseases. For example, injection of collagenase into the joints of mice results in lesions similar to osteoarthritis. P. M. van der Kraan, J. Exp. Path., (1990) 71:19–31. Emphysema is characterized by disruption of the alveolar walls and coalescence of the alveolar spaces. Mice made transgenic for a construct that expresses the collagenase gene in lung cells exhibited these symptoms. D'Armiento et al., supra. Epithelial organs, including the skin, have an outer epidermal layer, a basement membrane and a layer of dermis comprising a stroma that includes fibroblasts. Skin, in particular, is composed of stratified, squamous, keratinized epithelium, called the epidermis. Aged skin contains a greater number of senescent cells than young skin. Aged skin tends to be wrinkled, dry and scaly. Mice made transgenic for a construct that expresses the collagenase gene in skin took on characteristics of aged skin: Their skin was dry, wrinkled and scaly, and exhibited acanthosis, hyperkeratosis and epidermal hyperplasia. Also, the transgenic mice demonstrated increased susceptibility to tumorigenesis. J. D'Armiento et al., Molec. and Cell Biol., (1995) 15:5732–39.

Certain premature aging syndromes, such as Werner syndrome, are characterized by premature cellular senescence. Persons with Werner syndrome show hair and dermal thinning, atherosclerosis, osteoporosis and increased incidence of cancer.

Replicative senescence and its regulation are an increasingly active area of study. Genetic markers of senescence and methods of expressing genes in senescent cells or altering expression of genes in senescent cells would constitute advances in the art.

SUMMARY OF THE INVENTION

Nucleotide sequences between nucleotides –35 and –134, and, more specifically, between nucleotides –35 and –100 of the human interstitial collagenase gene promoter (SEQ ID NO: 1) have been found to contain elements responsible for much of the increased transcription of collagenase in senescent cells. These sequences are called the senescence responsive element, or "SnRE." Removal of the senescence responsive element from the collagenase promoter eliminates increased transcription from the promoter in senescent cells.

The interstitial collagenase gene promoter contains three known transcriptional regulatory elements: a PEA-3 (or ets) element at position –89 to –82; a CdxA element at –81 to –75; and an AP-1 element at position –72 to –66. Mutating the AP-1 site abolishes transcription in senescent cells. Mutating the PEA-3 site decreases promoter activity by about 40%. However, eliminating sequences upstream of the AP-1 site, e.g., upstream of nucleotide –77, also abolishes promoter activity.

Placing a senescence responsive element upstream of other promoters in a senescent cell results in increased transcription of genes to which it is operatively linked.

Accordingly, this invention provides a recombinant polynucleotide comprising an expression control sequence operatively linked to a heterologous nucleotide sequence, the expression control sequence comprising (1) a senescence responsive element and (2) a minimal promoter positioned downstream of the senescence responsive element, wherein the senescence responsive element up-regulates transcription of the heterologous nucleotide sequence in a senescent cell. In one embodiment, the minimal promoter is heterologous with respect to the senescence responsive element, e.g., it is not the intersitial collagenase gene minimal promoter. In another embodiment, the SnRE comprises nucleotides –89 to –66 of the interstitial collagenase gene promoter (5'-gaggatgtta taaagcatga gtca-3' (SEQ ID: NO: 1).

In another aspect, this invention provides a method for expressing a heterologous nucleotide sequence in a senescent cell comprising the step of providing the cell with a recombinant polynucleotide comprising an expression control sequence operatively linked to a heterologous nucleotide sequence, the expression control sequence comprising (1) a senescence responsive element and (2) a minimal promoter positioned downstream of the senescence responsive element, wherein the senescence responsive element up-regulates transcription of the heterologous nucleotide sequence in a senescent cell; and culturing the cell under conditions for expression.

In another aspect, this invention provides an isolated recombinant host cell comprising a recombinant polynucleotide comprising an expression control sequence operatively linked to a heterologous nucleotide sequence, the expression control sequence comprising (1) a senescence responsive element and (2) a minimal promoter positioned downstream of the senescence responsive element, wherein the senescence responsive element up-regulates transcription of the heterologous nucleotide sequence in a senescent cell.

In another aspect, this invention provides a transgenic non-human animal having a germ cell that comprises a recombinant polynucleotide comprising an expression control sequence operatively linked to a heterologous nucleotide sequence, the expression control sequence comprising (1) a senescence responsive element and (2) a minimal promoter positioned downstream of the senescence responsive element, wherein the senescence responsive element up-regulates transcription of the heterologous nucleotide sequence in a senescent cell.

In another aspect, this invention provides methods for monitoring senescence in a cell, cell population, tissue, organ or organism. In one embodiment, the method comprises the steps of culturing, under conditions for expression, a recombinant host cell of this invention; detecting or measuring the amount of expression of the reporter gene by the cell; and determining whether the measured amount is different than the amount expected in a pre-senescent cell. The difference between the measured amount and the expected amount reflects the degree to which the cell is senescent. In other embodiments, the methods comprise measuring the amount of, or detecting, expression of the reporter gene in a cell population, tissue, organ or organism comprising recombinant cells of the invention, and determining whether the amount of expression is different than an expected amount in the sample in a pre-senescent state.

In another aspect, this invention provides a method for determining whether a compound alters the activity of a senescence responsive element in a cell. The method comprises the steps of culturing, under conditions for expression; a recombinant cell of this invention; contacting the cell with the compound; measuring the amount of expression of the reporter polypeptide; and determining whether the measured amount is different than the amount expected from a recombinant host cell to which no compound has been administered. A difference between the measured amount and the expected amount indicates that the compound alters the activity of the senescence responsive element in the cell.

In another aspect, this invention provides a compound identified by the aforesaid method.

In another aspect, this invention provides a polynucleotide probe that specifically hybridizes with a contiguous nucleotide sequence within nucleotides −35 to −134 of the interstitial collagenase gene promoter, or with a sequence complementary to a contiguous nucleotide sequence within nucleotides −35 to −134 of the promoter.

In another aspect, this invention provides an inhibitory polynucleotide comprising an antisense sequence of at least 7 nucleotides that specifically hybridizes to a nucleotide sequence within nucleotides −35 to −134 of the interstitial collagenase gene promoter, or the complement of the promoter sequence, wherein the inhibitory polynucleotide inhibits transcription of nucleotide sequences operatively linked to expression control sequences comprising a senescence responsive element.

In another aspect, this invention provides a method of inhibiting in a cell the expression of a nucleotide sequence operatively linked to an expression control sequence that comprises a senescence responsive element, the method comprising the step of providing the cell with an inhibitory polynucleotide of this invention.

In another aspect this invention provides a pharmaceutical composition comprising a pharmaceutically acceptable carrier and a prophylactically or therapeutically effective amount of: (a) a recombinant polynucleotide comprising an expression control sequence operatively linked to a heterologous nucleotide sequence, the expression control sequence comprising (1) a senescence responsive element and (2) a minimal promoter positioned downstream of the senescence responsive element, wherein the senescence responsive element up-regulates transcription of the heterologous nucleotide sequence in a senescent cell; (b) a recombinant polynucleotide comprising expression control sequences operatively linked to a nucleotide sequence coding for the expression an inhibitory polynucleotide comprising nucleotides in a sequence substantially identical to or substantially complementary to a contiguous sequence of 6 nucleotides within nucleotides −35 to −134 of SEQ ID NO: 1, wherein the inhibitory polynucleotide inhibits transcription of nucleotide sequences operatively linked to expression control sequences comprising the senescence responsive element; or (c) an inhibitory polynucleotide comprising an antisense sequence of at least 7 nucleotides that specifically hybridizes to a nucleotide sequence within nucleotides −35 to −134 of the interstitial collagenase gene promoter, or the complement of the promoter sequence, wherein the inhibitory polynucleotide inhibits transcription of nucleotide sequences operatively linked to expression control sequences comprising a senescence responsive element.

In another aspect this invention provides methods of prophylactically or therapeutically treating a senescent condition in a subject. Therapeutic agents can be administered in the pharmaceutical preparations of this invention.

A method of treating a senescent condition associated with the activity of a senescence responsive element comprises the step of inhibiting the expression of a gene operatively linked to an expression control sequence that includes the senescence responsive element. Inhibiting expression of the gene provides a treatment of the senescent condition. Inhibiting expression can involve, for example, providing an inhibitory polynucleotide of the invention.

A method of prophylactically or therapeutically treating a senescent condition associated with under-expression of a gene comprises the step of providing cells of the subject with a recombinant polynucleotide comprising expression control sequences comprising a senescence responsive element operatively linked to the gene. Expression of the gene provides a treatment of the senescent condition.

In particular, this invention provides prophylactic and therapeutic methods of treating aged epithelium, cancers of the epithelium, and inflammatory diseases of the aged, such as osteoarthritis, Alzheimer's disease and atherosclerosis.

In another aspect this invention provides a method of determining whether a sample comprises a compound that binds to a senescence responsive element comprising contacting the sample with a polynucleotide probe of the invention; and determining whether a compound has bound to the probe. Binding indicates that the sample contains a compound that binds to the senescence responsive element.

BRIEF DESCRIPTION OF THE DRAWINGS

FIG. 3: The promoter region −35 to −134 contains the major determinant of the enhanced transcription in senescent cells. Deletion of this region (PGL 522Δ34/134 construct) resulted in a drastic decrease in the promoter activity in senescent cells.

FIG. 4: The nucleotide sequence of nucleotides −134 to −34 of the human interstitial collagenase promoter (SEQ ID NO: 1).

FIG. 5: The nucleotide sequence of the 5' un-transcribed regions of the human interstitial collagenase gene, including (SEQ ID NO:2). This sequence is from Angel et al., *Molec. and Cell Biol.*, (1987) 7:2256–66.

DETAILED DESCRIPTION OF THE INVENTION

I. DEFINITIONS

Figure 1:
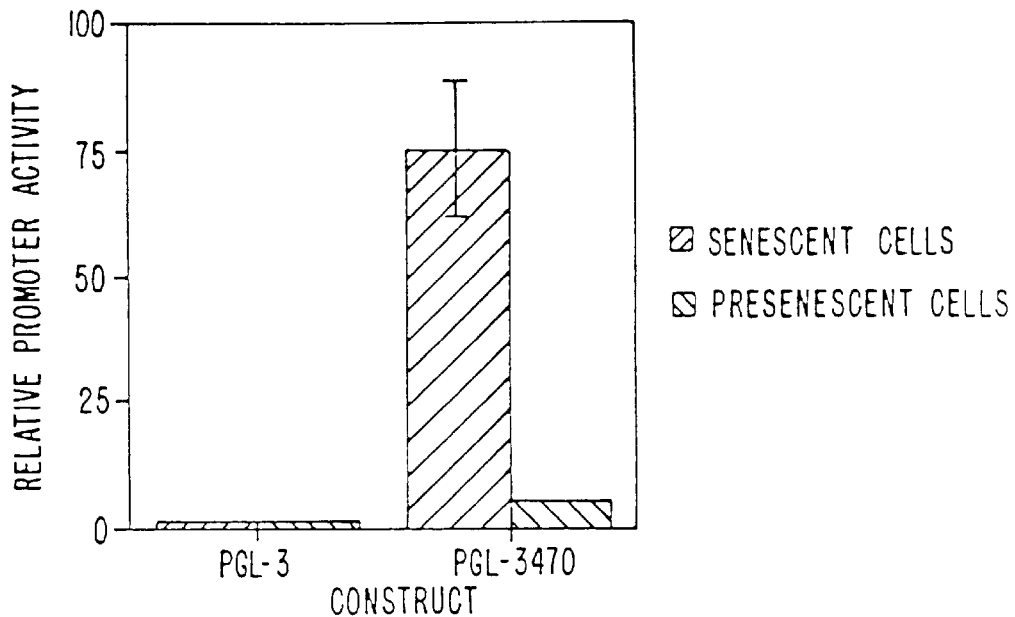
FIG. 1: Human interstitial collagenase is over-expressed in senescent human fibroblasts (WI-38) due to increased transcription initiation. The 3470 bp collagenase promoter driving the luciferase reporter (pGL-3470) was transfected into pre-senescent and senescent cells and reporter activity was measured 72 h later. Senescent cells expressed 15- to 20-fold more luciferase activity than pre-senescent cells. The promoter-less reporter vector (pGL3) was inactive in both cell types.
Figure 2:
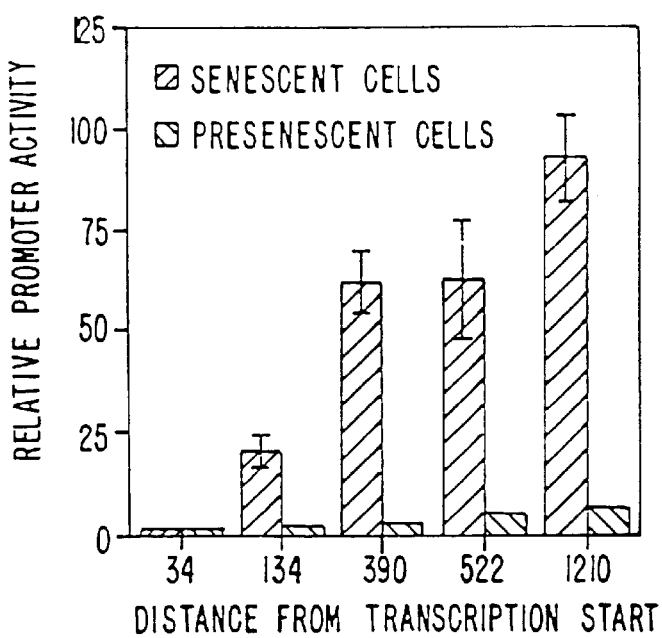
FIG. 2: The region between −35 and −100 (1=start of transcription) accounts for the largest increase in promoter activity in senescent cells. Several 5' deletions in the collagenase promoter in pGL-3470 were made, and the deletion vectors were transfected into pre-senescent and senescent cells. Deletion up to −134 resulted in a 3–4 fold reduction in promoter activity in senescent cells; deletion up to −34 resulted in a 20- to 25-fold reduction in promoter activity in senescent cells. All deletion constructs showed 10- to 15-fold less activity in pre-senescent cells.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2d ed. 1994); *The Cambridge Dictionary of Science and Technology* (Walker ed., 1988); and Hale & Marham, *The Harper Collins Dictionary of Biology* (1991). As used herein, the following terms have the meanings ascribed to them unless specified otherwise.

"Polynucleotide" refers to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide nucleic acids ("PNAs"), and the like. Such polynucleotides can be synthesized, for example, using an automated DNA synthesizer. "Nucleic acid" typically refers to large polynucleotides. "Oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Recombinant polynucleotide" refers to a polynucleotide having sequences that are not naturally joined together. An amnplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well. Appropriate unicellular hosts include any of those routinely used in expressing eukaryotic or mammalian polynucleotides, including, for example, prokaryotes, such as *E. coli*; and eukaryotes, including for example, fungi, such as yeast; and mammalian cells, including insect cells (e.g., Sf9) and animal cells such as CHO, R1.1, B-W, L-M, African Green Monkey Kidney cells (e.g. COS 1, COS 7, BSC 1, BSC 40 and BMT 10) and cultured human cells.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

A "reference sequence" is a defined sequence used as a basis for a sequence comparison and may be a subset of a larger sequence, e.g., a complete cDNA, protein, or gene sequence.

Because two polynucleotides or polypeptides each may comprise (1) a sequence (i.e., only a portion of the complete polynucleotide or polypeptide sequence) that is similar between the two polynucleotides, or (2) a sequence that is divergent between the two polynucleotides, sequence comparisons between two (or more) polynucleotides or polypeptides are typically performed by comparing sequences of the two polynucleotides over a "comparison window" to identify and compare local regions of sequence similarity.

A "comparison window" refers to a conceptual segment of typically at least 12 consecutive nucleotide or 4 consecutive amino acid residues that is compared to a reference sequence. The comparison window frequently is at least 15 or at least 25 nucleotides in length or at least 5 or at least 8 amino acids in length. The comparison window may comprise additions or deletions (i.e., gaps) of about 20 percent or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Dr., Madison, Wis.) or by inspection, and the best alignment (i.e., resulting in the highest percentage of homology over the comparison window) generated by any of the various methods is selected.

A subject nucleotide sequence or amino acid sequence is "identical" to a reference sequence if the two sequences are the same when aligned for maximum correspondence over the length of the nucleotide or amino acid sequence.

The "percentage of sequence identity" between two sequences is calculated by comparing two optimally aligned sequences over a comparison window, determining the number of positions at which the identical nucleotide or amino acid occurs in both sequences to yield the number of matched positions, dividing the number of matched positions by the total number of positions in the window of comparison (i.e., the window size), and multiplying the result by 100 to yield the percentage of sequence identity. Unless otherwise specified, the comparison window used to compare two sequences is the length of the shorter sequence.

When percentage of sequence identity is used in reference to polypeptides it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to known algorithm. See, e.g., Meyers & Miller, *Computer Applic. Biol. Sci.*, 4: 11–17 (1988); Smith & Waterman, *Adv. Appl. Math.* 2: 482 (1981); Needleman & Wunsch, *J. Mol. Biol.* 48: 443 (1970); Pearson & Lipman, *Proc. Natl. Acad. Sci. USA* 85: 2444 (1988); Higgins & Sharp *Gene*, 73: 237–244 (1988); Higgins & Sharp, *CABIOS* 5: 151–153 (1989); Corpet et al., *Nucleic Acids Research* 16: 10881–90 (1988); Huang et al., *Computer Applications in the Biosciences* 8: 155–65 (1992); and Pearson et al., *Methods in Molecular Biology* 24: 307–31 (1994). Alignment is also often performed by inspection and manual alignment.

A subject nucleotide sequence or amino acid sequence is "substantially identical" to a reference sequence if the subject amino acid sequence or nucleotide sequence has at least 80% sequence identity over a comparison window. Thus, sequences that have at least 85% sequence identity, at least 90% sequence identity, at least 95% sequence identity, at least 98% sequence identity or at least 99% sequence identity with the reference sequence are also "substantially identical." Two sequences that are identical to each other are, of course, also "substantially identical".

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Expression control sequence" refers to a nucleotide sequence in a polynucleotide that regulates the expression (transcription and/or translation) of a nucleotide sequence operatively linked to it. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Allelic variant" refers to any of two or more polymorphic forms of a gene occupying the same genetic locus. Allelic variations arise naturally through mutation, and may result in phenotypic polymorphism within populations. Gene mutations can be silent (no change in the encoded polypeptide) or may encode polypeptides having altered amino acid sequences. "Allelic variant" also refers to polymorphisms in non-coding sequences at a genetic locus and cDNAs derived from mRNA transcripts of genetic allelic variants, as well as the proteins encoded by them.

"Hybridizing specifically to" or "specific hybridization" or "selectively hybridize to," refers to the binding, duplexing, or hybridizing of a polynucleotide preferentially to a particular nucleotide sequence under stringent conditions when that sequence is present in a complex mixture (e.g., total cellular) DNA or RNA.

"Stringent conditions" refers to conditions under which a probe will hybridize preferentially to its target subsequence, and to a lesser extent to, or not at all to, other sequences. "Stringent hybridization" and "stringent hybridization wash conditions" in the context of polynucleotide hybridization experiments such as Southern and northern hybridizations are sequence dependent, and are different under different environmental parameters. An extensive guide to the hybridization of polynucleotides is found in Tijssen (1993) *Laboratory Techniques in Biochenmistry and Molecular Biology—Hybridization with Nucleic Acid Probes part I* chapter 2 "Overview of principles of hybridization and the strategy of nucleic acid probe assays", Elsevier, N.Y. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tin for a particular probe.

An example of stringent hybridization conditions for hybridization of complementary polynucleotides which have more than 100 complementary residues on a filter in a Southern or northern blot is 50% formalin with 1 mg of heparin at 42° C. with the hybridization being carried out overnight. An example of highly stringent wash conditions is 0.15M NaCl at 72° C. for about 15 minutes. An example of stringent wash conditions is a 0.2× SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1× SSC at 45° C. for 15 minutes. An example low stringency wash for a duplex of, e.g., more than 100 nucleotides, is 4–6× SSC at 40° C. for 15 minutes. In general, a signal-to-noise ratio of 2× (or higher) than that observed for an unrelated probe in the particular hybridization assay indicates detection of a specific hybridization.

A first sequence is an "antisense sequence" with respect to a second sequence if a polynucleotide whose sequence is the first sequence specifically hybridizes with a polynucleotide whose sequence is the second sequence.

"Reporter gene" refers to a gene that codes for the expression of a polynucleotide or polypeptide capable of acting as a label. Reporter genes include those encoding enzymes such as β-galactosidase, luciferase, secreted alkaline phosphatase and fluorescent proteins. e.g., green fluorescent protein.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or polynucleotides with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a polynucleotide having a complementary nucleotide sequence can be a part of a branched DNA molecule that is in turn detectable through hybridization with other labeled polynucleotides. Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a polynucleotide that hybridizes to one complementary sequence at the 5' end and to another complementary sequence at the 3' end, thus joining two non-complementary sequences.

"Amplification" refers to any means by which a polynucleotide sequence is copied and thus expanded into a larger number of polynucleotides, e.g., by reverse transcription, polymerase chain reaction, and ligase chain reaction.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Antibody" refers to a polypeptide substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Antibodies exist, e.g., as intact immunoglobulins or as a number of well characterized fragments produced by digestion with various peptidases. This includes, e.g., Fab' and F(ab)'$_2$ fragments. The term "antibody," as used herein, also includes antibody fragments either produced by the modification of whole antibodies or those synthesized de novo using recombinant DNA methodologies.

An antibody "specifically binds to" or "is specifically immunoreactive with" a protein when the antibody functions in a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Immunoassay" refers to an assay that utilizes an antibody to specifically bind an analyte. The immunoassay is characterized by the use of specific binding properties of a particular antibody to isolate, target, and/or quantify the analyte.

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide binding partner of the second polynucleotide. Thus, the polynucleotide whose sequence 5'-TATAC-3' is complementary to a polynucleotide whose sequence is 5'-GTATA-3'.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutainine (Q);
4) Arginine (R), Lysine (K);
5) Isoleucine (I), Leucine (L), Methionine (M), Valine (V); and
6) Phenylalanine (F), Tyrosine (Y), Tryptophan (W).

"Substantially pure" means an object species is the predominant species present (i.e., on a molar basis, more abundant than any other individual organic biomolecular species in the composition), and a substantially purified fraction is a composition wherein the object species comprises at least about 50% (on a molar basis) of all organic biomolecular species present. Generally, a substantially pure composition means that about 80% to 90% or more of the organic biomolecular species present in the composition is the purified species of interest. The object species is purified to essential homogeneity (contaminant species cannot be detected in the composition by conventional detection methods) if the composition consists essentially of a single organic biomolecular species. "Organic biomolecule" refers to an organic molecule of biological origin, e.g., proteins, polynucleotides, carbohydrates or lipids. Solvent species, small molecules (<500 Daltons), stabilizers (e.g., BSA), and elemental ion species are not considered organic biomolecular species for purposes of this definition.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally-occurring.

"Pharmaceutical composition" refers to a composition suitable for pharmaceutical use in a mammal. A pharmaceutical composition comprises a pharmacologically effective amount of an active agent and a pharmaceutically acceptable carrier. "Pharmacologically effective amount" refers to that amount of an agent effective to produce the intended pharmacological result. "Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in *Remington's Pharmaceutical Sciences*, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, or intravenous intraperitoneal injection; or topical, transdermal, or transmucosal administration).

A population of cells is "senescent" if, after incubating a sub-confluent population of the cells with $^3$H-thymidine for about 72 hours, the percentage of cells with labelled nuclei is below about 20%. A population of cells is "pre-senescent" if after the same treatment, at least 70% of the nuclei are stained. A cell is "senescent" if, after incubating the cell with $^3$H-thymidine for about 72 hours, cell nucleus is not labelled or is insignificantly labeled compared with cells of a pre-senescent cell population so treated.

Apart from these defining terms, senescent cell populations also can be identified by using bromodeoxyuridine, rather than $^3$H-thymidine, as the label, and detecting incorporation with anti-BrdU antibodies. Senescent cell populations also are characterized by an inability to undergo at least one population doubling when maintained in optimal growth media for four weeks.

A "senescent phenotype" or "senescent condition" is a phenotype or condition of senescent cells that differs from pre-senescent cells (e.g., increased collagenase expression), or a phenotype or condition of tissues, organs or organisms in which the action of senescent cells is a necessary component (e.g., traits of aged skin).

A "senescence responsive element" ("SnRE") is a nucleotide sequence identical or substantially identical to a nucleotide sequence located upstream of nucleotide –33 of the interstitial collagenase gene promoter that, in a senescent cell, up-regulates transcription of nucleotide sequences operatively linked to the promoter.

"Interstitial collagenase gene promoter" or "IC promoter" refers to the nucleotide sequence from nucleotide –1 to about nucleotide –500 of SEQ ID NO:2, as well as allelic forms thereof. A nucleotide sequence encoding the interstitial collagenase gene and 5' flanking sequence is further described in Burke et al., supra.

An element "up-regulates" transcription of a nucleotide sequence if transcription of a nucleotide sequence operatively linked to an expression control sequence including the element is greater than transcription of the nucleotide sequence operatively linked to the same expression control sequence excluding the element by a statistically significant amount.

"Minimal promoter" refers to expression control sequences that are necessary to engage the core polymerase, but not sufficient to drive transcription of a gene. The interstitial collagenase gene minimal promoter is located within nucleotides –1 to –34 of SEQ ID NO:2 and includes a TATA box. A minimal promoter is "heterologous" with respect to the senescence responsive element if it has no more than ten sequential nucleotides from nucleotides –1 to –34 of SEQ ID NO:2 between the initiation codon and the senescence responsive element. The CMV minimal promoter, the RSV minimal promoter, and the adenoviral late minimal promoter are examples of heterologous minimal promoters.

An expression control sequence is "essentially free of upstream sequences of the interstitial collagenase promoter" if sequences up to 500 nucleotides upstream of the senescence responsive element have less than 50% sequence identity over a window of 20 nucleotides with sequences of the interstitial collagenase promoter upstream from nucleotide –134 of SEQ ID NO: 1.

A nucleotide sequence is "heterologous" if it is not operatively linked with a senescence responsive element in nature. The interstitial collagenase gene is known to be operatively linked with the senescence responsive element in nature.

"Germ cell" refers to sperm cells or oocytes.

II. RECOMBINANT POLYNUCLEOTIDES COMPRISING THE SENESCENCE RESPONSIVE ELEMENT

This invention provides recombinant polynucleotides comprising an expression control sequence that includes (1) a senescence responsive element and (2) a minimal promoter positioned downstream of the senescence responsive element, in which the expression control sequence is operatively linked to a heterologous nucleotide sequence. The senescence responsive element is derived from the interstitial collagenase gene promoter. This promoter includes three transcriptional elements, PEA-3 (–89 to –82), CdxA (–81 to –75) and AP-1 (–72 to –66). Senescence responsive elements for use in the recombinant polynucleotides of the invention generally will include one or more of the elements PEA-3, CdxA and AP-1.

PEA-3 elements bind nuclear factors that share a common DNA-binding domain: the ets domain. Ets transcription factors comprise a family of related proteins, some of which have a helix-turn-helix domain (Wasylyk, B., et al. (1993) *Eur. J. Biochem.* 211:7–18). A tandem arrangement of ets and AP-1 sites has been documented in certain other promoters (Majerus, M. A., et al. (1992) *Nucleic Acids Res.* 20:2699–2703).

CdxA is a binding site for a homeobox transcription factor. Y. Margalite et al., (1993) *Nucl. Res.* 21:4915–22. Its sequence is usually given as the complementary stand sequence to the sequence described here, i.e., 5'-ctttata-3'.

AP-1 and ets transcription factors are known to interact to activate the promoters of a variety of genes. S. K. Logan et al. (1996) *J. Biol. Chem.* 271:774–782; A. G. Bassuk et al. (1995) *Immunity* 3:223–237; S. Bergelson et al. (1994) *Biochem. Biophys. Res. Commun.* 200:290–297; and A. Gutman et al. (1990) *EMBO Journal* 9:2241–2246.

While not wishing to be limited by theory, it is believed that an interaction between the PEA-3 and AP-1 elements, mediated by protein binding to the CdxA element is responsible for up-regulation by the senescence responsive element.

The SnRE used in the invention can comprise, for example, a sequence of at least 8 nucleotides, at least 15 nucleotides, at least 24 nucleotides, at least 30 nucleotides; at least 50 nucleotides; at least 65 nucleotides; or 100 nucleotides substantially identical or identical to a nucleotide sequence from nucleotides –134 to –35 of the IC gene promoter (from SEQ ID NO: 1). In various embodiments, the SnRE can comprise any of the following sequences from the IC gene promoter (all from SEQ ID NO: 1) as well as combinations (e.g., nucleotides –134 to –66) and fragments:

Nucleotides –89 to –66:
  5'-aggatgtta taaagcatga gtca-3';
Nucleotides –95 to –60:
  5'-aatcaa gaggatgtta taaagcatga gtcagacacc-3';
Nucleotides –100 to –50:
  5'-tagctaatcaa       gaggatgtta       taaagcatga gtcagacacc tctggctttc-3';
Nucleotides –100 to –35:
  5'-tagctaatcaa gaggatgtta taaagcatga gtcagacacc tctggctttc tggaagggca aggac-3';
Nucleotides –134 to –35:
  5'-agtc accatttcta atgattgcct agtctattca tagctaatcaa gaggatgtta taaagcatga gtcagacacc tctggctttc tggaagggca aggac-3'.

The recombinant polynucleotide generally will have the structure: 5'—senescence responsive element—minimal promoter—transcription initiation codon—sequence coding for expression of heterologous protein—transcription termination codon—transcription termination and polyadenylation sequence—3'. The recombinant polynucleotide is capable of increasing transcription of the nucleotide sequence in senescent cells and, in particular, fibroblasts. The sequence of the 5' upstream flanking sequence is presented in FIG. 5 (SEQ ID NO:2), from Angel et al., *Molec. and Cell Biol.*, (1987) 7:2256–66. The entire coding sequence can be found in G. I. Goldberg et al., "Human fibroblast collagenase," *J. Biol. Chem.*, (1986) 261:6600–6605. The organization of the gene is described in Collier et al. "Structure of the human skin fibroblast collagenase gene," *J. Biol. Chem.* 263:10711–13 (1988).

Preferably, the senescence responsive element is placed just upstream of the minimal promoter. For example, the senescence responsive element can be attached essentially directly to the 5' end of the minimal promoter, no more than about 50 nucleotides upstream from the minimal promoter, or no more than about 100 nucleotides upstream from the minimal promoter.

In one embodiment, the recombinant polynucleotide utilizes sequences from the interstitial collagenase promoter. For example, the expression control sequences can comprise the interstitial collagenase minimal promoter, and, additionally, the senescence responsive element and sequences of several hundred nucleotides of the 5' flanking region, i.e., upstream from the initiation codon of the interstitial collagenase gene. This can include, for example, several thousand nucleotides of the 5' flanking region or fewer than about 500 nucleotides of the 5' flanking region.

In other embodiments, the expression control sequences comprise the senescence regulatory element and a heterologous minimal promoter, and/or is essentially free of upstream sequences of the interstitial collagenase promoter. The minimal promoter can be from any promoter known in the art including, for example, the adenoviral late promoter, the CMV promoter, the RSV promoter, the metallothionein promoter or the SV40 promoter.

The heterologous nucleotide sequence can code for the expression of a reporter polypeptide. Such constructs are useful to measure expression of a gene in a cell or to determine whether the cell is senescent. In this instance, the expression control sequence can comprise the interstitial collagenase promoter. Alternatively, the embodiment, the heterologous nucleotide sequence can code for the expression of polypeptides or functional polynucleotides whose expression one wishes to increase in senescent cells. For example, transcription regulators, interleukin-6, tissue inhibitors of metalloproteinases ("TIMPs"), collagens, elastin, growth regulatory transcription factors (e.g., E2F, c-fos, Id genes), and certain apoptosis regulators (e.g., hax) all are expressed in lowered quantities in senescent cells, in contrast to pre-senescent cells. The activities of certain cyclin-dependent kinase activities also are lower in senescent cells. Telomerase is not expressed in most somatic cells of most mammals. Therefore, the heterologous polynucleotide could code for expression of the RNA component or polypeptide components of telomerase. The RNA component of human telomerase is described in J. Feng et al., "The RNA Component of Human Telomerase," (1995) *Science* 269:1236–1241 and Villeponteau et al., U.S. Pat. No. 5,583, 016. Other molecules tend to be over-expressed in senescent cells. These include, for example, collagenase, metalloproteinases, plasminogen activators, inhibitors of plasminogen activators, interleukin-1, insulin-like growth factors, inhibitors of cyclins or cyclin-dependent kinases. Accordingly, the heterologous nucleotide sequence can encode an inhibitor of these factors.

The polynucleotides used in the present invention can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide can be isolated by polymerase chain reaction of human genomic DNA using primers based on known DNA sequences. A wide variety of cloning and in vitro amplification methodologies are well-known to persons of skill. PCR methods are described in, for example, U.S. Pat. No. 4,683,195; Mullis et al. (1987) *Cold Spring Harbor Symp. Quant. Biol.* 51:263; and Erlich, ed., *PCR Technology*, (Stockton Press, N.Y., 1989). Polynucleotides also can isolated by screening genomic libraries with probes selected from the sequences of SEQ ID NO:1 under stringent hybridization conditions, e.g., salt and temperature conditions substantially equivalent to 5× SSC and 65° C. for both hybridization and wash.

Mutant versions of the senescence regulatory element can be made by site-specific mutagenesis or by random mutagenesis caused by increasing the error rate of PCR of the original polynucleotide with 0.1 mM $MnCl_2$ and unbalanced nucleotide concentrations.

This invention provides expression vectors, e.g., recombinant polynucleotides further comprising expression control sequences operatively linked to the nucleotide sequence coding for expression of the polypeptide. Expression vectors are be adapted for function in eukaryotes by inclusion of appropriate promoters, replication sequences, markers, etc. The construction of expression vectors and the expression of genes in transfected cells involves the use of molecular cloning techniques also well known in the art. Sambrook et al., *Molecular Cloning—A Laboratory Manual*, Cold Spring Harbor Laboratory, Cold Spring Harbor, N.Y., (1989) and *Current Protocols in Molecular Biology*, F. M. Ausubel et al., eds., (Current Protocols, a joint venture between Greene Publishing Associates, Inc. and John Wiley & Sons, Inc., (most recent Supplement).

Methods of transfecting genes into mammalian cells and obtaining their expression for in vitro use or for gene therapy, are well known to the art. See, e.g., *Methods in Enzymology*, vol. 185, Academic Press, Inc., San Diego, Calif. (D. V. Goeddel, ed.) (1990) or M. Krieger, *Gene Transfer and Expression—A Laboratory Manual*, Stockton Press, New York, N.Y., (1990).

Expression vectors useful in this invention depend on their intended use. Such expression vectors must, of course, contain expression and replication signals compatible with the host cell. Expression vectors useful in this invention include viral vectors such as retroviruses, adenoviruses and adeno-associated viruses, plasmid vectors, cosmids, liposomes and the like. Viral and plasmid vectors are preferred for transfecting mammalian cells.

In another embodiment, endogenous genes are transcribed by operatively linking them to expression control sequences supplied endogenously that recombine with genomic DNA. In one method, one provides the cell with a recombinant polynucleotide containing a targeting sequence, which permits homologous recombination into the genome upstream of the transcriptional start site of target gene; the expression control sequences; an exon of the target gene; and an unpaired splice-donor site which pairs with a splice acceptor in the target gene. Such methods are discussed in Treco et al., WO 94/12650; Treco et al., WO 95/31560 and Treco et al., WO 96/29411.

III. METHODS OF USING RECOMBINANT POLYNUCLEOTIDES COMPRISING THE SENESCENCE RESPONSIVE ELEMENT

Recombinant polynucleotides comprising the senescence responsive element are useful for expressing the heterologous nucleotide sequences operatively linked to them in animal cells and, in particular, in mammalian cells. For model systems, the mammal can be a small mammal such as a rodent (e.g., a mouse) or a rabbit. In therapeutic methods, the mammal can be a human or any mammal treated in veterinary medicine. More particularly, the recombinant polynucleotides are useful for obtaining increased expression of these nucleotide sequences in senescent cells. This expression is achieved by transfecting a cell with the recombinant polynucleotides of the invention. The expression control sequences are, of course, chosen to function in the recombinant host cell.

A. Isolated, Recombinant Host Cells

Accordingly, the invention also provides recombinant host cells comprising recombinant polynucleotides of this invention. The cells can be senescent cells, mixed passage cells, or pre-senescent cells. However, increased expression is expected in senescent cells. Many cell types can be transfected with these recombinant polynucleotides, including those cells known to express collagenase, especially fibroblasts (e.g., lung or skin), epithelial cells, stromal cells or any non-terminally differentiated cell.

Isolated recombinant host cells are useful in vitro to study the effect of increased gene expression on senescent cells. When the gene is a reporter gene, the cells are useful in screening methods to identify compounds that inhibit the activity of the senescence responsive element. They also are useful for administration into a subject for genetic therapy.

In animal subjects, in vivo transfection of cells with a recombinant polynucleotide of the invention is useful to restore levels of gene expression in senescent cells.

B. Transgenic Non-human Animals

Recombinant polynucleotides comprising the senescence responsive element also are useful for preparing transgenic animals whose senescent cells express the heterologous nucleotide sequence in greater amounts than in pre-senescent cells. Accordingly, this invention also provides transgenic non-human animals having a germ cell that comprises a recombinant polynucleotide of this invention. The animal can be a mammal. Such animals are useful in the study of senescence. For example, the heterologous nucleotide sequence can encode a reporter gene. Cells of the animal can be examined at various points in its life to determine whether the cells are senescent or not. Cell from various organs can be tested to determine whether the organs senescent at the same rate. Compounds can be administered to the animal to determine what effect they have on senescence.

In one embodiment, the non-human mammal further comprises germ cells comprising a recombinant polynucleotide comprising second expression control sequences operatively linked to a second nucleotide sequence coding for expression of, for example, a collagenase inhibitor, a p21 inhibitor, a cyclin dependent kinase, a p53 tumor suppressor or a retinoblastoma tumor suppressor.

The transgenic animals of this invention are usually produced by introducing the recombinant polynucleotide into a fertilized oocyte or embryonic stem (ES) cell, typically by microinjection, electroporation, lipofection, particle-minediated gene transfer. The transgenic animals express the heterologous nucleotide sequence in tissues depending upon whether the promoter is inducible by a signal to the cell, or is constitutive. Transgenic animals can be bred with non-transgenic animals to produce transgenic animals with mixed characteristics.

Using standard methods, transgenic mice have been produced that include recombinant polynucleotides having either nucleotides −34 to +34 of the IC gene promoter operatively linked with a β-galactosidase reporter gene, or −134 to +34 of the IC gene promoter operatively linked with a β-galactosidase reporter gene. The transgenic mice integrated into their genome the construct containing the expression control sequences including a senescence responsive element.

C. Expression Assays

Recombinant polynucleotides comprising the senescence responsive element also are useful in a variety of assays involving detection of the expression of reporter genes in senescent cells. Such assays are useful to determine whether a cell is senescent, because senescent cells will exhibit higher expression of such reporter genes than pre-senescent cells.

In one aspect, this invention provides methods of identifying senescent cells in a population or in an organism involving providing recombinant host cells harboring a recombinant polynucleotide of the invention that comprises the senescence responsive element operatively linked with a reporter gene, or providing a transgenic non-human animal whose cells comprise a reporter gene operatively linked with the senescence responsive element. Then, the amount of expression of the reporter gene is determined under selected conditions. This amount is compared with a control amount that reflects the expected amount of expression in a pre-senescent cell. Thus, the amount measured in the test cell reflects whether the cell is senescent or not. The assay can be run on populations of cells to determine the percent of senescent cells in the population. The cells can be isolated, recombinant cells in vitro, cells transfected ex vivo and introduced into the animal, or cells of a transgenic animal. Thus, the vector is introduced into the cells to be tested.

D. Screening Assays

In another aspect, this invention provides screening methods to identify compounds that alter the activity of the senescence responsive element. The methods involve providing a recombinant host cell transfected with a recombinant polynucleotide comprising an expression control sequence operatively linked to a reporter gene, wherein the expression control sequence comprises a senescence responsive element located upstream of a minimal promoter; or providing a transgenic non-human animal whose cells comprise a reporter gene operatively linked with the senescence responsive element. Then, the cell or animal is exposed to a test compound. The amount of expression of the reporter gene is determined and compared with a control amount. If the amount of expression is different than the control amount, then the compound alters the activity of the senescence responsive element.

Frequently, the reporter will be an enzyme. Methods of assaying for reporters are well known in the art and generally include exposing a sample to a substrate for the enzyme and determining the amount or rate at which the enzyme catalyzes the substrate. The amount of expression in single cells can be measured if the signal provided by the reporter is visible, such as a fluorescent signal. For example, if the heterologous nucleotide sequence encodes a fluorescent protein, such as green fluorescent protein, fluorescence in a single cell can be detected and measured using, for example, a fluorescent cell sorter. See, e.g., Heim et al., WO 96/23810.

IV. POLYNUCLEOTIDE PROBES

This invention is also directed to polynucleotide probes, preferably isolated, that specifically hybridize with a nucleotide sequence of SEQ ID NO:1 or its complement. The probes typically have at least 15 nucleotides, at least 20 nucleotides or at least 25 nucleotides. The probes can have a sequence identical to or complementary to the sequence of SEQ ID NO:1. In one embodiment, the probes are no more than about 50 nucleotides in length. In one embodiment, the isolated polynucleotides further comprise a label. These isolated polynucleotides are useful as primers for amplification of senescence responsive element sequences by, e.g., PCR. They also are useful as probes in hybridization assays, such as Southern and Northern blots, for identifying polynucleotides having a nucleotide sequence of a protein of this invention. Probes of this invention that hybridize with the senescence responsive element are useful as inhibitory polynucleotides to suppress expression of nucleotide sequences operatively linked with the senescence responsive element. Polynucleotide probes can be introduced into a cell by any of the means already described. Polynucleotide probes can be made by any means known to the art including, for example, chemical synthesis, PCR and expression from expression vectors.

V. CONSTRUCTS AND METHODS FOR INHIBITING THE ACTIVITY OF THE SENESCENCE RESPONSIVE ELEMENT

A. Inhibitory Polynucleotides

Nucleotide sequences operatively linked to the senescence responsive element are over-expressed in senescent cells. This invention provides constructs and methods for inhibiting the expression of such nucleotide sequences using inhibitory polynucleotides. Inhibitory polynucleotides are single-stranded polynucleotides that can inhibit the function of a target nucleotide sequence. Without wishing to be limited by theory, inhibitory polynucleotides may function by hybridizing to the polynucleotide they inhibit. Typically, an inhibitory polynucleotide has at least about 55% sequence identity over a stretch of at least 6–25 nucleotides (e.g., 6, 10, 15, 20 or 25), preferably at least about 65%, more preferably at least about 75%, and most preferably at least about 90%. See M. Kanehisa, *Nucleic Acids Res.* (1984) 12:203.

By binding to the appropriate target sequence, a DNA-DNA, DNA-RNA or RNA-DNA duplex is formed. Certain of these polynucleotides are termed "antisense" because they are usually complementary to the sense, or coding, strand of the gene. Recently, approaches for use of "sense" inhibitory polynucleotides have also been developed. The term "inhibitory polynucleotides" as used herein, refers to both "sense" and "antisense" polynucleotides.

By binding to the target polynucleotide, the inhibitory polynucleotide can inhibit the function of the target polynucleotide. This could, for example, be a result of blocking DNA replication or DNA transcription, e.g., by interfering with the attachment of the polymerase to the promoter; interfering with processing of, poly(A) addition to, or translation of mRNA; or promoting inhibitory mechanisms of the cells, such as promoting RNA degradation. Inhibitory polynucleotide methods therefore encompass a number of different approaches to altering expression of specific genes that operate by different mechanisms. These different types of inhibitory polynucleotide technology are described in C. Helene and J. Toulme, (1990) *Biochinm. Biophys. Acta.*, 1049:99–125.

Inhibitory polynucleotide approaches can be classified into those that target DNA sequences, those that target RNA sequences (including pre-mRNA and mRNA), those that target proteins (sense strand approaches), and those that cause cleavage or chemical modification of the target polynucleotides.

Approaches targeting DNA fall into several categories. Polynucleotides can be designed to bind to the major groove of the duplex DNA to form a triple helical or "triplex" structure. Alternatively, inhibitory polynucleotides are designed to bind to regions of single stranded DNA resulting from the opening of the duplex DNA during replication or transcription. Helene and Toulme, supra.

The inhibitory polynucleotides can also be targeted against mRNA. In this approach, the inhibitory polynucleotides are designed to hybridize to a target sequence in the mRNA and, thereby, interfere with its translation. Translation of mRNA is inhibited if there is a measurable decrease in the amount of protein produced by the cell after treatment. Inhibiting translation of an mRNA results in suppression of the cellular function carried out by the encoded protein. For example, an inhibitory polynucleotide complementary to regions of c-myc mRNA inhibits c-myc protein expression in a human promyelocytic leukemia cell line, HL60, which over-expresses the c-myc proto-oncogene. See E. L. Wickstrom et al., (1988) *PNAS (USA)*, 85:1028–1032 and Harel-Bellan et al., (1988) *Exp. Med.*, 168:2309–2318. Maier et al., (1990) *Science*, 249:1570–74 showed how to suppress interleukin-1α activity using unmodified antisense oligonucleotides. As described in Helene and Toulme, supra, inhibitory polynucleotides targeting mRNA have been shown to work by several different mechanisms in order to inhibit translation of the encoded protein(s).

Whatever the ultimate strategy, it is desirable to provide oligomers with physiological properties which render them more effective. The general approach to constructing various polynucleotides useful in inhibitory polynucleotide therapy has been reviewed by A. R. Vander Krol et al. (1988), *Biotechniques* 6:958–976, and by C. A. Stein et al., (1988) *Cancer Res.* (1988) 48:2659–2668. See also *Oligodeoxynucleotides: Antisense Inhibitors of Gene Expression*, Cohen, J. S., editor, MacMillan Press, London, pages 79–196 (1989), and Antisense RNA and DNA, (1988), D. A. Melton, Ed., Cold Spring Harbor Laboratory, Cold Spring Harbor, N.Y.

B. Delivery Of Inhibitory Polynucleotides

This invention contemplates a variety of means for delivering the inhibitory polynucleotide to the cell including, for example, direct uptake of the molecule by the cell from solution, facilitated uptake through liposome vectors and intracellular expression from an expression cassette.

One can provide a cell with an inhibitory polynucleotide by contacting the cell with a soluble inhibitory polynucleotide, for example, in the culture medium in vitro or in the circulatory system, interstitial fluid or tissue mass in vivo. Soluble inhibitory polynucleotides present in the external milieu have been shown to gain access to the cytoplasm.

One also can provide inhibitory polynucleotides by expressing them inside a cell using expression vectors having an expression control sequence operatively linked to a nucleotide sequence that encodes the inhibitory polynucleotide. The nucleotide sequence hybridizes with a sequence identical to or complementary to at least 6 nucleotides within nucleotides −35 to −134 of SEQ ID NO:1. The sequence can be no more than 30 nucleotides.

VI. PROPHYLACTIC AND THERAPEUTIC TREATMENTS

A. Treating Senescent Phenotypes and Conditions

The activity of senescent cells differs from pre-senescent cells and results in certain of the senescent phenotypes or conditions characteristic of aged cells, tissues, organs and organisms. Certain of the senescent phenotypes result from over-expression of genes under the transcriptional control of senescence responsive elements, while others result from under-expression of genes. Accordingly, these phenotypes can be prevented, diminished or reversed by decreasing expression of over-expressed genes by interfering with the activity of genes already under the transcriptional control of a senescence responsive element, or by increasing expression of under-expressed genes by putting them under the control of a senescence responsive element. The phenotypes can be treated in aged subjects, subjects suffering from a pro-geriatric disease, such as Werner's syndrome or Hutchinson-Guilford syndrome, among others, or in non-aged subjects for prophylaxis.

Genes over-expressed in senescent cells, such as the interstitial collagenase gene, are under the control of a senescence responsive element. Two senescent phenotypes associated with over-expression of interstitial collagenase are aged stroma underlying epithelial organs and epithelial cancers. Epithelial organs include, for example, skin, lung, stomach, intestine, pancreas, kidney, blood vessels, and liver. Aged epithelial organs are characterized by a loss in function and in integrity of the stroma and epithelium. For example, skin exhibits wrinkling, loss of elasticity, and dryness resulting at least in part from breakdown of collagen.

Increased risk of cancer also is a senescent phenotype. Senescent fibroblasts secrete high levels of collagenase and stromelysin, which tend to destroy the dermal matrix. This destruction alters the micro-environment of epithelial cells. Senescent fibroblasts also secrete high levels of heregulin, a ligand for an erbB receptor. Heregulin stimulates the growth of epithelial tumors that have an amplification of the erbB2 gene. It is believed that as a result of the destruction of the dermal matrix, these initiated epithelial cells can become cancerous, separate from the epithelium and metastasize. Thus, an age-dependent accumulation of senescent cells in mitotic tissues creates a pro-carcinogenic environment.

More generally, it is believed that other senescent phenotypes result from over-expression of genes under the control of a senescence responsive element. For example, the aged tend to have a general increase in inflammation. This appears to result at least in part from the over-expression of inflammatory mediators. Diseases of the aged that include an inflammatory component include, for example, osteoarthritis (inflammation of the joints), Alzheimer's disease (inflammation of the brain) and atherosclerosis (inflammation of the blood vessels).

Accordingly, treatments involve targeting cells of the subject that over-express the gene which is a factor in the phenotype with an agent that inhibits expression of genes operatively linked to the IC gene promoter. More particularly, the agent can interfere with the activity of the senescence responsive element. For example, in the treatment of aging skin or prophylaxis of cancer, epithelial cells, and, in particular, fibroblasts, can be targeted.

Certain genes are under-expressed in senescent cells. Up-regulating these genes is useful in therapies to restore function diminished from under-expression. For example, IL-6 is under-expressed in senescent cells. IL-6 is produced by monocytes, macrophages, $T_H 2$ cells and bone marrow stromal cells. It promotes differentiation of into plasma cells and stimulates antibody secretion. Therefore, up-regulating IL-6 production in senescent cells is useful in restoring certain immune system functions.

B. Therapy With Polynucleotides

The recombinant polynucleotides of this invention are useful in gene therapy. In one aspect, recombinant polynucleotides that have expression control sequences comprising the senescence responsive element are useful for expressing genes in senescent cells. In particular, such expression vectors are useful for expressing genes that are under-expressed or that are not expressed in senescent cells, or simply for expressing genes at high levels in these cells.

In another aspect, one can deliver inhibitory polynucleotides or recombinant polynucleotides that code for the expression of inhibitory polynucleotides to a cell.

Host cells can be transfected by any methods known to the art. For example, methods for retroviral transfection are described in, for example, M. Krieger (33) and *Methods in Enzymology*, Vol. 185 (34). Cells can be transfected with plasmid vectors, for example, by electroporation. Cells can be transfected by recombinant polynucleotides by calcium phosphate precipitation DNA liposome complexes or by particle-mediated gene transfer (biolistics). Methods are also known for transfection of polynucleotides using liposomes.

C. Pharmaceutical Compositions

The therapeutic polynucleotides can be delivered by any route and in any suitable vehicle. The agent of the invention molecule can be administered to the subject in a pharmaceutical composition comprising a pharmaceutically acceptable carrier and a pharmacologically effective amount the agent of the invention. A pharmacologically effective amount of the agent of the invention depends upon the intended result, e.g., expression of a nucleotide sequence from the senescence responsive element or inhibition of the senescence responsive element with an inhibitory polynucleotide.

The pharmaceutical compositions are intended for all well known forms of administration and, in particular, parenteral administration for prophylactic and/or therapeutic treatment. Local administration, such as transdermally, also is contemplated. The pharmaceutical compositions can be administered in a variety of unit dosage forms depending upon the method of administration. For example, unit dosage forms for parenteral administration include unit doses of injectable solutions.

The agent of the invention can be administered by any means known in the art for delivery of proteins. However, systemic administration by injection is preferred. This includes intramuscular, intravenous, intraperitoneal, and subcutaneous injection.

The form, amounts and timing of administration generally are a matter for determination by the practitioner. In one embodiment, the pharmaceutical composition is delivered as a unit dosage form. Dosages include about of $10^7$ to $10^{13}$ particles of viral vector per ml of carrier. The volume administered can be selected by the practitioner. According to one embodiment of this invention, approximately $10^{10}$ vectors suspended in about 1 ml of sterile PBS constitute a therapeutically effective amount.

VII. ISOLATING MOLECULES THAT BIND TO THE SENESCENCE RESPONSIVE ELEMENT

Polynucleotides comprising sequences for the senescence responsive element are useful in screening methods to identify molecules that bind to the element and through which it may function. One such method involves screening a phage-based human fibroblast cDNA library with a labeled polynucleotide probe of the invention. In another method a yeast strain is created containing recombinant polynucleotides comprising a recombinant polynucleotide having expression control sequences comprising tandem senescence responsive elements and a minimal promoter operatively linked to a heterologous nucleotide sequence encoding a selection or reporter gene. A human cDNA library fused to a yeast transcription activator domain is then used to select human cDNAs that bind the senescence responsive element. In another method, such molecules can be isolated by creating affinity matrices to which the probe is attached. The test sample is exposed to the matrix, and molecules that bind the senescence responsive element are isolated.

The following examples are offered by way of illustration, not by way of limitation.

EXAMPLES

I. MAPPING THE SENESCENCE RESPONSIVE ELEMENT

A. Materials and Methods

WI-38 human fetal lung fibroblasts were used at 60–80% confluence. For all experiments, the growth potential of each culture was determined by labeling sub-confluent cells with $^3$H-thymidine for 72 h and counting the fraction of cells with labeled nuclei (LN) after autoradiography. In general, senescent cells had less than 10% LN, whereas pre-senescent cells had greater than 70% LN. The data shown are typically the average of three to five independent experiments, with each data point being the average of duplicates.

A Pst I restriction fragment from the plasmid pCLCAT3 (Frisch et al., *Oncogene*, 1990, 5:75) contained 3.4 kb of the 5' flanking sequence of the human interstitial collagenase gene. This fragment encompassed position +37 to position −3470, where position +1 is the start of transcription. The fragment was inserted into the Pst I site in the multiple cloning site of the vector pBluescript II KS (+) from Stratagene (La Jolla, Calif.). This generated the plasmid pIC-1.

Restriction of pIC-1 with Kpn I and Bam HI yielded a fragment containing the promoter region up to position −521. This fragment was cloned into the luciferase reporter vector pGL3-basic (Promega Corp., Madison, Wis.) between the Ipn I and Bgl II sites. This construct was named pGL-522 because it contained the 5' flanking region of the human interstitial collagenase from positions +37 to position −522 (having reconstituted the Kpn I site). pGL-522 served as the basis for all the other reporter constructs, so that all constructs shared a common 3' end of the collagenase promoter.

pGL-3470 was constructed by cutting pIC-1 with Kpn I, recovering the 3 kb fragment, and cloning it into the Kpn I site of pGL-522. Restriction of pGL-3470 with Eco RI, recovery of the largest fragment and self-ligation of this fragment produced the construct pGL-3030. Restriction of pGL-3470 with Eco RV and Pvu II, recovery of the largest fragment and self-litigation of this fragment produced pGL-2490. Digestion of pGL-3470 with Eco RI and Bgl II, end-filling, recovery of the largest fragment and self-ligation generated pGL-1210.

Pfu DNA polymerase was used in the polymerase chain reaction to amplify from pGL-522 three DNA fragments using the following primers:

1) 5' ccaaataatc tgctagcagt caccatttct aatgattgcc (SEQ ID NO:3)
2) 5' ggctttctgg aagggcaacg cgtctatata tacagaggga gc (SEQ ID NO:4)
3) 5' gtttttggcg tcttccatgg tggctttacc (SEQ ID NO:5)
4) 5' gcgcagtgtt aggaattcca ccctctgccc (SEQ ID NO:6)

Primers 1 and 3 were used to generate an Nhe I-Nco I fragment, primers 2 and 3 were used to generate an Mlu I-Nco I fragment, and primers 3 and 4 were used to generate an Eco RI-Nco I fragment. After digesting the amplified fragments with the appropriate restriction endonucleases, they were cloned into pGL3-basic (cut with Nhe I/Nco I or Mlu I/Nco I) or PGL-3400 (cut with Eco RI and Nco I; the largest restriction fragment was recovered). This gave rise to the constructs pGL-134 (containing nucleotides −134 to +37), pGL-34 (containing nucleotides −34 to +37) and PGL-390 (containing nucleotides −390 to +37), respectively. The construct PGL-522 Δ34/134 contained the collagenase promoter up to position −522 but with the region between positions −34 and −134 deleted. This was constructed by amplifying a fragment from PGL-522 using the following primers:

5) 5' aatagggtac caggcagctt aacaaaggc (SEQ ID NO:7)
6) 5' agaaatggtg acgcgtagca gattatttgg aatcactt (SEQ ID NO:8)

This fragment, containing the Kpn I and Mlu I sites, was cloned into PGL-34 cut with the same enzymes.

Cells were transfected by electroporation using Cytomix buffer (van den Hoff et al., 1992, Nucl Acids Res 20:2902). The composition of the buffer is as follows: 120 mM KCl, 0.15 mM $CaCl_2$, 10 mM $K_2HPO_{4,\ 10}$ mM $KH_2PO_{4,\ 25}$ mM HEPES, 2 mM EGTA, 5 mM $MgCl_2$ (pH adjusted to 7.6 with KOH). Cytomix was made fresh or stored frozen, to avoid precipitation of the salts. Immediately prior to electroporation, 2 mM ATP and 5 mM glutathione was added and the pH was readjusted to 7.6.

WI-38 cells were trypsinized, washed with DME medium and spun at low speed in a bench-top centrifuge. The cell pellets were washed with 10 ml of fresh cytomix buffer and counted with a Coulter counter. $1 \times 10^6$ senescent cells were used for each electroporation. Pre-senescent cells were used at $3 \times 10^5$ up to $1 \times 10^6$. The cells were spun again at low speed, and then resuspended in enough fresh cytomix buffer (containing ATP and glutathione) to provide 400–500 µl cell suspension per cuvette (Biorad 0.4 cm electrode gap).

Plasmid DNA was added to the cuvettes, and the suspension was mixed gently and incubated on ice for at least 5 min. Using the luciferase PGL 3 reporter system (Promega Corp., Madison, Wis.), 1 µg of the reporter plasmid easily yielded measurable activity of the collagenase gene promoter in senescent cells. 0.5–1 µg of a β-galactosidase reporter gene driven by the human CMV promoter (CMV-βGAL) was included to control for transfection efficiency. CMV=βGAL yielded readily measurable activity using a chemiluminescent β-galactosidase assay (Clontech, Palo Alto, Calif.).

Senescent cells were electroporated at 240–270 V and 950 µF using a Biorad Gene Pulser II apparatus. Pre-senescent cells were electroporated at 300 V, 950 µF. Before delivering the pulse, the sample resistance was measured to confirm that the resistance was 20 ohms.

After the pulse was delivered, the cuvettes were placed on ice. As soon as all cuvettes were pulsed, the electroporated cells were seeded in 35 mm dishes containing DME medium plus 10% fetal calf serum and incubated at 37° C. for I h. Because most of the electroporated cells formed floating clumps, at 1 h intervals, a sterile pipette was used to gently pipet the medium, being careful not to dislodge cells that had already attached, in order to break up the cell clumps. This operation was repeated three or four times until most cells attached to the dish. After 6–12 h the medium was replaced with fresh DME containing 10% fetal calf serum.

The transfected cells were cultured for 72 h from the start of electroporation, then lysed to extract protein and assay luciferase and β-galactosidase activity. Luciferase was from assayed using a kit from Promega (Madison, Wis.), and the reporter Lysis Buffer to prevent inhibition of β-galactosidase activity. β-galactosidase activity was determined using a Luminescent β-galactosidase assay system from Clontech (Palo Alto, Calif.). The luciferase activity was divided by the β-galactosidase activity in each sample to calculate a normalized luciferase activity. The normalized luciferase activity reflects the transcriptional activity of the collagenase promoter fragments, normalized for any cuvette-to-curette variation in transfection efficiency or toxicity due to the electroporation.

B. Localization of Senescence Responsive Element Activity to Nucleotides −34 to −134

Reporter constructs PGL-34, PGL-134, PGL-390, PGL-522, PGL-522 delta 34/134 and PGL-1210 were tested for activity in senescent cells. FIG. 3 shows the results. Most of the sequence responsible for transcription in senescent cells mapped to nucleotides −34 to −134. More particularly, PGL-134 showed a 20.8-fold increase in transcription compared with the minimal promoter, PGL-34. Adding the nucleotides −135 to −522 increased transcription about another 4-fold. However, removal of nucleotides −34 to −134 from PGL-522 (PGL-522 delta 34/134) reduced transcription to only about 3-fold over the minimal promoter.

C. Localization Of Senescence Responsive Element Activity To Nucleotides −34 to −100

Reporter constructs linking short fragments of the collagenase promoter to a luciferase gene were transfected into pre-senescent and senescent human fibroblasts (WI-38 cells). These mapping experiments localized the SnRE to a 66 bp region between positions −34 and −100.

TABLE I

| Construct | Fold activity over minimal promoter |
| --- | --- |
| PGL-34 | 1 +/− 0.5 |
| PGL-77 | 4.1 +/− 1.7 |
| PGL-100 | 27.5 +/− 6 |
| PGL-134 | 29.6 +/− 8 |

D. Role Of PEA-3 And AP-1 Elements In Senescence Responsive Element Activity

A construct lacking the PEA-3 site, but containing the AP-1 site (i.e., terminating at position −77), failed to drive reporter activity in senescent cells. By contrast, the construct extending up to position −100, which included both the PEA-3 and AP-1 sites, exhibited 93% of the activity of the largest construct tested in this experiment (up to position −134). This result indicates that sequences around the PEA-3 site are necessary for SnRE activity.

Two additional luciferase reporter constructs, one carrying a mutated PEA-3 site and a wild type (wt) AP-1 site and a second carrying a mutated AP-1 site flanked by a wt PEA-3 site were transfected into senescent WI-38 fibroblasts. The sequences of the wild type and the mutant sites are given below:

```
wt PEA-3 + wt AP-1:
          -89       -82            -72    -66
             agaggatgtt ataaagcatg agtca       (SEQ ID NO:9)
                PEA-3      CdxA      AP-1 mutant PEA-3 + wt AP-1:
             agagtactttt ataaagcatg agtca      (SEQ ID NO:10)
                *   ** wt PEA-3 + wt AP-1:
             agaggatgtt ataaagcatg agtcagac    (SEQ ID NO:11)
                PEA-3      CdxA      AP-1 wt PEA-3 + mutant AP-1
             agaggatgtt ataaagcagg attccttac   (SEQ ID NO:12)
                                *   *  **
```

Mutations in the AP-1 site completely abolished reporter activity. This result indicates that the AP-1 site is necessary for SnRE activity.

Mutations in the PEA-3 site reduced promoter activity, albeit not as strongly as mutations in the AP-1 site, resulting in a 40% decrease in activity. This results suggests that the PEA-3 site at least partially contributes to SnRE activity. Combined with the deletion experiment described above, the results further suggest that the CdxA site also is involved in SnRE activity. The data indicate that the PEA-3, CdxA and AP-1 sites are required for optimal activity of the collagenase promoter in senescent cells.

TABLE II

| Construct | Fold activity over minimal promoter |
| --- | --- |
| PGL-34 | 1.0 +/− 0.6 |
| PGL-100 (wt PEA3/wt AP1) | 26.0 +/− 6.7 |
| PGL-100 (wt PBA3/mut AP1) | 1.3 +/− 0.4 |
| PGL-100 (mut PEA3/wt AP1) | 16.0 +/− 5 |

II. SENESCENCE RESPONSIVE ELEMENT ACTIVITY IN PRE-SENESCENT AND SENESCENT CELLS

A. Active versus Quiescent Cells

Previous experiments showed that SnRE was active in senescent cells maintained in 10% serum, but not in pre-senescent cells growing in 10% serum. It was possible that differences in SnRE activity between pre-senescent and senescent cells reflected differences in their growth states, rather than differences in their replicative potentials. Pre-senescent WI-38 fibroblasts were made quiescent by depriving them of serum for 4 days, and used to determine whether the SnRE was also active in quiescent cells. These experiments showed that activity of the collagenase promoter up to position −522 was not significantly higher in quiescent cells, compared to actively growing cells.

TABLE III

| | Fold activity over minimal promoter | |
| --- | --- | --- |
| Construct | Growing Cells | Quiescent Cells |
| PGL-34 | 1.0 +/− 0.2 | 1.0 +/− 0 |
| PGL-134 | 2.3 +/− 0.7 | 2.7 +/− 0.85 |
| PGL-522 | 2.6 +/− 0.7 | 3.6 +/− 1.5 |

B. Senescent versus Pre-senescent Cells

Bacterial β-galactosidase (βgal) reporter vectors were constructed in order to determine SnRE activity in individual cells.

The CMV promoter was excised from pCMVβ (Clontech) and was either recircularized (generating a promoterless plasmid) or ligated to the −34/+37 or −134/+37 fragments from the human interstitial collagenase promoter. The constructs thus obtained were called PO (promoterless), P-34 (collagenase promoter lacking the SnRE) and P-134 (collagenase promoter containing the SnRE), respectively. PO and P-34 served as controls to rule out the existence of cryptic senescence activated promoters or enhancers in the vector.

Heterogeneous cultures of primary mouse embryo fibroblasts and human fibroblasts were transfected. Mouse cultures contained roughly 50% pre-senescent/50% senescent cells, whereas the human cultures contained 25% pre-senescent/75% senescent cells. After transfection, the cells were cultured for 72 h in medium containing tritiated thymidine. The cells were then fixed and incubated with the βgal substrate X-gal, which stains βgal-expressing cells blue. After staining, the cells were subjected to autoradiography, which identifies cells that underwent DNA synthesis during the labeling period (incorporated radiolabel into nuclei).

Experiments show that only pre-senescent cells show nuclear radiolabeling; senescent cells do not synthesize DNA and therefore do not label with tritiated thymidine. If the SnRE is active preferentially in senescent cells, the majority of reporter-positive (blue) cells should be devoid of radiolabel. Thus, this experiment distinguishes senescent from pre-senescent cells by nuclear labeling, and, in the same cells, determines whether or not the SnRE is active. The pooled results of several such experiments are shown below.

TABLE IV

Mouse Fibroblasts: Ave. labeling index = 56.5% (53%–60%)

| Construct | Number of Blue Cells Detected | % Labeled Nuclei | Blue Cells with Labeled Nuclei | Blue Cells, % Labeled Nuclei |
|---|---|---|---|---|
| None | 0 | 56.5 | Not Applicable | Not Applicable |
| P0 | 1 | | 0 | Not Significant |
| P-34 | 4 | | 1 | Not Significant |
| P-134 | 669 | | 64 | 9.6 |

TABLE V

Human Fibroblasts: Ave. labeling index = 23.5% (14.8–34%)

| Construct | Number of Blue Cells Detected | % Labeled Nuclei | Blue Cells with Labeled Nuclei | Blue Cells, % Labeled Nuclei |
|---|---|---|---|---|
| None | 0 | 23.5 | Not Applicable | Not Applicable |
| P0 | 1 | | 0 | Not Significant |
| P-34 | 5 | | 1 | Not Significant |
| P0134 | 338 | | 25 | 7.4 |

PO (promoterless vector) and P-34 (vector containing the collagenase minimal promoter only) were essentially incapable of driving βgal reporter expression. Cells expressing reporter activity (blue cells) were abundant only in cultures transfected with vector in which the SnRE was present upstream of the collagenase minimal promoter.

Most cells in which the SnRE was active (blue cells) did not incorporate tritiated thymidine (<10% labeled nuclei). By contrast, the bulk of the cell population had a much higher labeling index (53–60% for mouse cultures, and 14–34% for human cultures). Because cells were incubated with radiolabel for 3 days prior to staining for βgal (SnRE) activity, this experiment overestimates the number of radiolabeled cells showing SnRE activity. Thus, the SnRE was preferentially active in (unlabeled) senescent fibroblasts, and this was true of both mouse and human fibroblasts.

β-galactosidase activity itself was not responsible for the lack of DNA synthesis βgal-positive cells. Pre-senescent human fibroblasts expressing pCMVβgal (β-galactosidase under control of the CMV promoter) synthesized DNA to similar extends as untransfected cells or cells transfected with a control vector.

Most of the cells with an active SnRE (blue cells) had a large, flattened morphology characteristic of senescent cells.

C. Activity Of Stably Integrated Senescence Responsive Element

The experiments described above utilized transiently transfected plasmids, the majority of which do not integrate into the genome. In this experiment, PGL3 or PGL-134 and a plasmid carrying a neomycin resistance gene were co-transfected into HCA-2 human neonatal foreskin fibroblasts. PGL3 lacks a promoter upstream of the luciferase reporter gene. PGL-134, by contrast, contains the region +37 to −134 of the collagenase promoter, which contains the SnRE, upstream of the reporter gene. Stable transfectants were selected by growing the cells in a neomycin-related drug (G-418). Only one stably transfected clone from each transfection had sufficient replicative potential to test reporter (luciferase) activity as the cells approached senescence. Cells were monitored for replicative potential, as judged by the percent nuclei that incorporated tritiated thymidine in 72 hours (% Labeled Nuclei), and luciferase activity (RLU, relative luminescence units). As the cells lost replicative potential, SnRE (luciferase) activity increased.

TABLE VI

| | PGL3 | | | PGL-134 | | |
|---|---|---|---|---|---|---|
| % Labeled Nuclei | RLU/ mg protein | Fold Increase | | % Labeled Nuclei | RLU/ mg protein | Fold Increase |
| 33 | 683 | 1.0 | | 55 | 1162 | 1.0 |
| 27 | 310 | 0.5 | | 38 | 3175 | 2.7 |
| 5 | 205 | 0.3 | | 14 | 10138 | 8.7 |

III. THE SNRE CONFERS SENESCENCE-DEPENDENT RESPONSIVENESS TO A HETEROLOGOUS PROMOTER

Experiments demonstrate that SnRE confers senescence-dependent regulation on a heterologous promoter. Plasmid pADβ (Clontech, Palo Alto, Calif.) contains the minimal promoter from the major late genes of adenovirus 2 linked to a βgal reporter gene. Nucleotides −34 to −134 of the interstitial collagenase gene promoter was cloned upstream of the minimal promoter in pADβ to generate pADβSNRE. Primary mouse embryo fibroblasts were transfected with pADβ and pADβSNRE, labeled for 72 h with tritiated thymidine, and assayed for labeled nuclei and βgal activity. The results of several experiments are shown below.

TABLE VII

Mouse Fibroblasts: Ave. labeling index = 65.1%

| Construct | Number of Blue Cells Detected | % Labeled Nuclei | Blue Cells with Labeled Nuclei | Blue Cells, % Labeled Nuclei |
|---|---|---|---|---|
| None | 0 | 65.1 | Not Applicable | Not Applicable |
| pADβ | 5 | | 0 | Not Significant |
| pADβSNRE | 1011 | | 182 | 18.0 |

The present invention provides a novel transcriptional regulator in senescent cells methods of using it. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A recombinant polynucleotide comprising an expression control sequence operatively linked to a heterologous nucleotide sequence, the expression control sequence comprising (1) a senescence responsive element comprising a sequence from the interstitial collagenase gene promoter (SEQ ID NO:2), wherein the sequence from the interstitial collagenase gene promoter includes at least 8 consecutive nucleotides from 5'-gaggatgtta taaagcatga gtca-3' (nucleotides 439 to 462 of SEQ ID: NO:2 and terminates on its 3' end no further than nucleotide 478 of SEQ ID NO:2, and (2) a heterologous minimal promoter positioned downstream of the senescence responsive element, wherein the senescence responsive element up-regulates transcription of the heterologous nucleotide sequence in a senescent cell.

2. The recombinant polynucleotide of claim 1 wherein the sequence from the interstitial collagenase gene promoter comprises nucleotides 439 to 462 of the interstitial collagenase gene promoter (5'-gaggatgtta taaagcatga gtca -3' (SEQ ID: NO:2)) and terminates on its 3' end no further than nucleotide 468 of SEQ ID NO:2.

3. The recombinant polynucleotide of claim 2 wherein the sequence from the interstitial collagenase gene promoter comprises nucleotides 428 to 462 of the interstitial collagenase gene promoter (5'-tagctaatcaa gaggatgtta taaagcatga gtca -3' (SEQ ID: NO:2)).

4. The recombinant polynucleotide of claim 2 wherein the sequence comprises nucleotides 394 to 462 of the interstitial collagenase gene promoter (5'-agtc accatttcta atgattgcct agtctattca tagctaatcaa gaggatgtta taaagcatga gtca -3' (SEQ ID: NO:2)).

5. The recombinant polynucleotide of claim 1 wherein the heterologous nucleotide sequence codes for the expression of a transcription regulator, interleukin-6, a tissue inhibitor of a metalloproteinase, collagen, elastin, a growth regulatory transcription factor, an apoptosis regulator or a protein or RNA component of telomerase.

6. The recombinant polynucleotide of claim 1 wherein the heterologous nucleotide sequence codes for the expression of an inhibitor of collagenase, an inhibitor of a metalloproteinase, a plasminogen activator, an inhibitor of a plasminogen activator, interleukin-1 receptor antagonist, an insulin-like growth factors, a cyclin or a cyclin-dependent kinase.

7. The recombinant polynucleotide of any of claims 1, 2, 3 and 4 wherein the sequence terminates on its 5' end no further than nucleotide 394 of SEQ ID NO:2.

8. A polynucleotide probe that specifically hybridizes with a contiguous nucleotide sequence of at least 6 nucleotides within nucleotides 394 to 478SEQ ID NO:2) of the interstitial collagenase gene promoter, or with a contiguous sequence of at least 6 nucleotides complementary to a contiguous nucleotide sequence within nucleotides 394 to 478 (SEQ ID NO:2) of the promoter.

9. The polynucleotide probe of claim 8 further comprising a label.

10. The polynucleotide probe of claim 8 comprising a sequence identical to or complementary to a contiguous nucleotide sequence of at least 6 nucleotides within nucleotides 394 to 478 (SEQ ID NO:2) of the interstitial collagenase gene promoter.

11. The polynucleotide probe of claim 8 comprising a sequence identical to or complementary to a contiguous nucleotide sequence of at least 6 nucleotides within nucleotides 428to 462 (SEQ ID NO:2) of the interstitial collagenase gene promoter.

12. The polynucleotide probe of claim 8 comprising a sequence identical to or complementary to a contiguous nucleotide sequence of at least 6 nucleotides within nucleotides 439 to 462 (SEQ ID NO:2) of the interstitial collagenase gene promoter.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
       (A) LENGTH: 101 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:1:

```
AGTCACCATT TCTAATGATT GCCTAGTCTA TTCATAGCTA ATCAAGAGGA TGTTATAAAG      60

CATGAGTCAG ACACCTCTGG CTTTCTGGAA GGGCAAGGAC T                        101
```

(2) INFORMATION FOR SEQ ID NO:2:

(i) SEQUENCE CHARACTERISTICS:
       (A) LENGTH: 698 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:2:

```
AATAGGGTAC CAGGCAGCTT AACAAAGGCA GAAGGGAACC TCAGAGAACC CCGAAGAGCC      60

ACCGTAAAGT GAGTGCTGGG GGAGCTGAAC TTCAGTCAGT ACAGGAGCCG AACAGCCATC     120

AGGTGCGCAG TGTTAGTAAT TCCACCCTCT GCCCTGGGAG CAAGGTGTGT GGAGAAACCT     180

GTAGCACTTT ATGACCATCA GAACCAGCCT TTTTCAAAAA GACCATGGAG TACTCTTTGA     240

CCTGTGTATA TAACAAGAAC CTTTCTCAAA TAGGAAAGAA ATGAATTGGA GAAAACCACT     300

GTTTACATGG CAGAGTGTGT CTCCTTCGCA CACATCTTGT TTGAAGTTAA TCATGACATT     360

GCAACACCAA GTGATTCCAA ATAATCTGCT AGGAGTCACC ATTTCTAATG ATTGCCTAGT     420

CTATTCATAG CTAATCAAGA GGATGTTATA AAGCATGAGT CAGACACCTC TGGCTTTCTG     480

GAAGGGCAAG GACTCTATAT ATACAGAGGG AGCTTCCTAG CTGGGATATT GGAGCAGCAA     540

GAGGCTGGGA AGCCATCACT TACCTTGCAC TGAGAAAGAA GACAAAGGCC AGTATGCACA     600

GCTTTCCTCC ACTGCTGCTG CTGCTGTTCT GGGGTGTGGT GTCTCACAGC TTCCCAGCGA     660

CTCTAGAAAC ACAAGAGCAA GATGTGGACT TAGTCCAG                            698
```

(2) INFORMATION FOR SEQ ID NO:3:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (ii) MOLECULE TYPE: DNA (genomic)

(xi) SEQUENCE DESCRIPTION: SEQ ID NO:3:

```
CCAAATAATC TGCTAGCAGT CACCATTTCT AATGATTGCC                           40
```

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GGCTTTCTGG AAGGGCAACG CGTCTATATA TACAGAGGGA GC         42

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

GTTTTTGGCG TCTTCCATGG TGGCTTTACC                       30

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GCGCAGTGTT AGGAATTCCA CCCTCTGCCC                       30

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

AATAGGGTAC CAGGCAGCTT AACAAAGGC                        29

(2) INFORMATION FOR SEQ ID NO:8:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

AGAAATGGTG ACGCGTAGCA GATTATTTGG AATCACTT              38

(2) INFORMATION FOR SEQ ID NO:9:

(i) SEQUENCE CHARACTERISTICS:
        (A) LENGTH: 25 base pairs
        (B) TYPE: nucleic acid -continued

```
            (C) STRANDEDNESS: single
            (D) TOPOLOGY: linear (ii) MOLECULE TYPE: DNA (genomic)

(xi) SEQUENCE DESCRIPTION: SEQ ID NO:9:

AGAGGATGTT ATAAAGCATG AGTCA                                              25

(2) INFORMATION FOR SEQ ID NO:10:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

AGAGTACTTT ATAAAGCATG AGTCA                                              25

(2) INFORMATION FOR SEQ ID NO:11:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

AGAGGATGTT ATAAAGCATG AGTCAGAC                                           28

(2) INFORMATION FOR SEQ ID NO:12:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

AGAGGATGTT ATAAAGCAGG ATTCCTAC                                           28
```